United States Patent
Jensen et al.

(10) Patent No.: US 9,925,280 B2
(45) Date of Patent: Mar. 27, 2018

(54) HYPERPOLARIZED AMINO ACIDS

(71) Applicant: BRACCO IMAGING S.P.A., Milan (IT)

(72) Inventors: Pernille Rose Jensen, Vaerlose (DK); Magnus Karlsson, Malmo (SE); Mathilde H. Lerche, Frederiksberg C (DK)

(73) Assignee: BRACCO IMAGING S.P.A., Milan (IT)

( * ) Notice: Subject to any disclaimer, the term of this patent is extended or adjusted under 35 U.S.C. 154(b) by 371 days.

(21) Appl. No.: 14/389,404

(22) PCT Filed: Mar. 28, 2013

(86) PCT No.: PCT/EP2013/056696
§ 371 (c)(1),
(2) Date: Sep. 30, 2014

(87) PCT Pub. No.: WO2013/149935
PCT Pub. Date: Oct. 10, 2013

(65) Prior Publication Data
US 2015/0118159 A1    Apr. 30, 2015

(30) Foreign Application Priority Data
Apr. 2, 2012 (EP) .................................. 12162792

(51) Int. Cl.
*A61K 49/10* (2006.01)
*C07C 231/12* (2006.01)

(52) U.S. Cl.
CPC ............ *A61K 49/10* (2013.01); *C07C 231/12* (2013.01)

(58) Field of Classification Search
None
See application file for complete search history.

(56) References Cited

U.S. PATENT DOCUMENTS

2008/0287774 A1    11/2008    Katz-Brull

FOREIGN PATENT DOCUMENTS

| EP | 0905685 A1 | 3/1999 |
|---|---|---|
| WO | 88/010419 A1 | 12/1988 |
| WO | 1990-000904 A1 | 2/1990 |
| WO | 1991-012024 A1 | 8/1991 |
| WO | 1993-002711 A1 | 2/1993 |
| WO | 1996-039367 A1 | 12/1996 |
| WO | 1998-010419 A1 | 3/1998 |
| WO | 1999-035508 A1 | 7/1999 |
| WO | 2002-037132 A1 | 5/2002 |
| WO | 2007-064226 A2 | 6/2007 |
| WO | 2008-086534 A1 | 7/2008 |
| WO | 2009-098191 A2 | 8/2009 |

OTHER PUBLICATIONS

Colombo Serra, Sonia et al. "Hyperpolarized 13C-labelled anhydrides as DNP precursors of metabolic MRI agents", Contrast Media & Molecular Imaging, 2012, 7, pp. 469-477, John Wiley & Sons, Ltd.
European Search Report for application No. EP12162792.1, dated Aug. 28, 2012.
Gallagher, Ferdia A. et al., "13C MR Spectroscopy Measurements of Glutaminase Activity in Human Hepatocellular Carcinoma Cells Using Hyperpolarized 13C-Labeled Glutamine", Magnetic Resonance in Medicine, vol. 60, No. 2, Aug. 1, 2008, pp. 253-257, XP055035925, ISSN: 0740-3194, DOI: 10.1002.
PCT International Search Report & Written Opinion for PCT/EP2013/056696, dated Jun. 3, 2013.
PCT International Preliminary Report on Patentability for PCT/EP2013/056696, dated Oct. 16, 2014.

*Primary Examiner* — Michael G Hartley
*Assistant Examiner* — Jennifer Lamberski
(74) *Attorney, Agent, or Firm* — Vivicar Law, PLLC

(57) ABSTRACT

Method for manufacturing a hyperpolarized amino acid, in particular glutamine, which substantially limits the formation of by-products, with respect to conventional aqueous preparations of sodium hydroxide with amino acids. The amino acid is in particular admixed with the hydroxide in the substantial absence of water and the dry mixture is dissolved in an anhydrous solvent in the presence of a polarizing agent. The obtained mixture is then subjected to a DNP process and can be used in metabolic MR imaging.

23 Claims, 1 Drawing Sheet

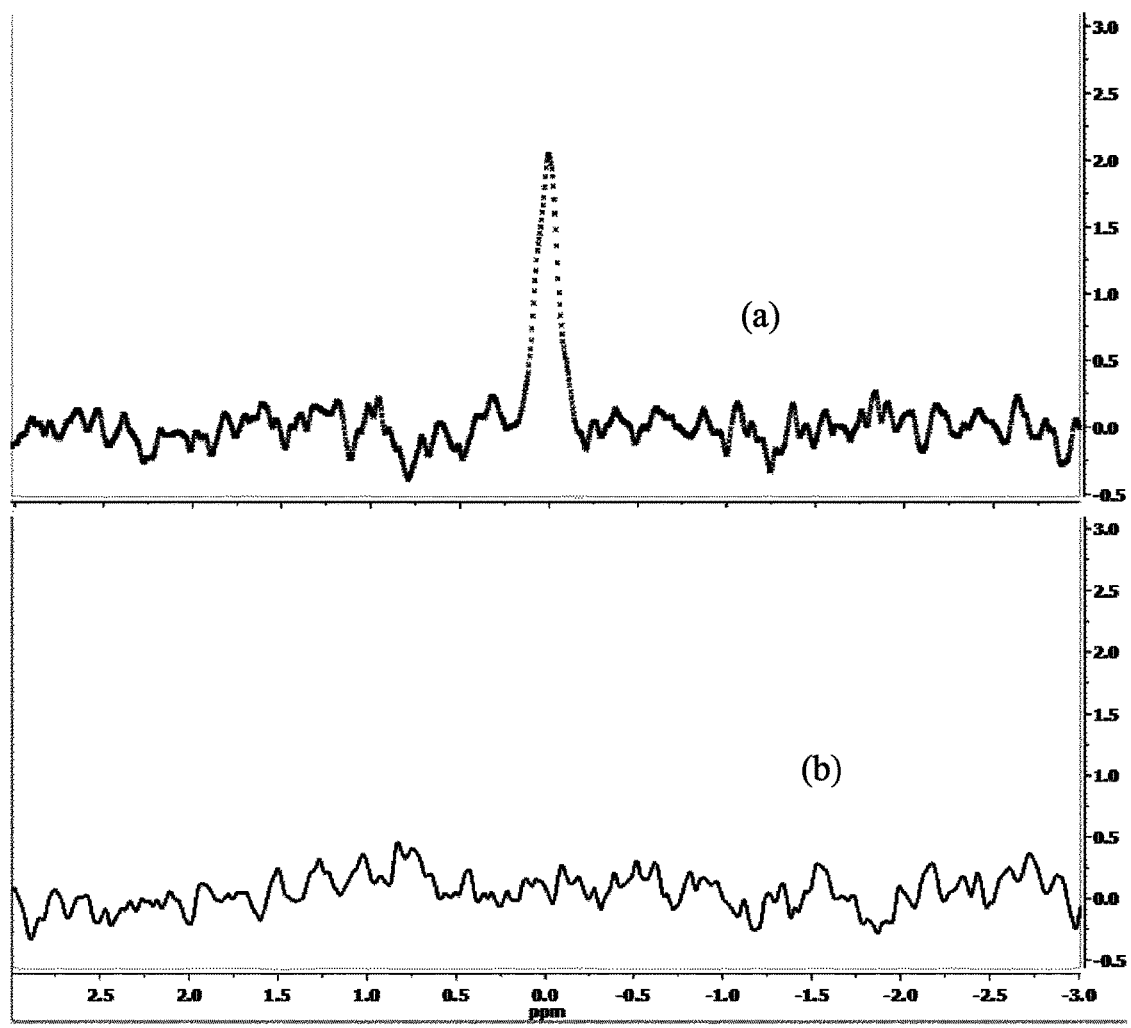

HYPERPOLARIZED AMINO ACIDS

CROSS-REFERENCE TO RELATED APPLICATIONS

This application is the national stage application of corresponding international application number PCT/EP2013/056696, filed Mar. 28, 2013, which claims priority to and the benefit of European application no. 12162792.1, filed Apr. 2, 2012, all of which are hereby incorporated by reference in their entirety.

TECHNICAL FIELD

The invention relates to a method for hyperpolarizing amino acids, particularly glutamine, and their use as magnetic resonance (MR) imaging agents.

BACKGROUND OF THE INVENTION

MRI is a non-invasive technique with broad diagnostic value. The technique has gained wide clinical acceptance and is of great importance in diagnostic medicine. However, despite significant technological advancements (increasing field strength and improvement in technology), applications of MRI are limited by an intrinsically low sensitivity.

Some alternatives to enhance its sensitivity have been developed which involve ex-vivo nuclear spin polarisation of agents, prior to administration and consequent in-vivo MR signal measurement.

WO 99/35508 describes a method for obtaining hyperpolarized high T1 agents by dynamic nuclear polarization (DNP). Intermediate molecules of metabolic cycles, including amino acids, are mentioned among the hyperpolarized high T1 agents, which can be used for in vivo imaging of metabolic activity; amino acids are mentioned among these molecules.

WO 2009/098191 describes a method for preparing hyperpolarized amino acids which comprises preparing a DNP mixture (i.e. a mixture suitable for undergoing DNP) of carboxylate salts of the amino acid by admixing the amino acid with an aqueous solution of an alkali metal or earth alkali metal hydroxide.

The Applicant has however observed that when the above method is used for hyperpolarizing amino acids comprising an additional non-terminal amino group in the molecule (glutamine in particular), formation of undesirable by-products of said amino acids are observed in the DNP mixture.

The applicant has now found a new method for preparing a DNP mixture comprising glutamine, which substantially reduces or avoids the above drawbacks.

SUMMARY OF THE INVENTION

An aspect of the invention relates to a method for manufacturing hyperpolarized glutamine, which comprises the steps of:

a) preparing a mixture comprising: (i) glutamine, (ii) $Rb^+$ or $Cs^+$ hydroxide, (iii) a polarizing agent and (iv) an anhydrous solvent;

b) subjecting the mixture of step a) to a dynamic nuclear polarization (DNP) process to obtain a hyperpolarized mixture comprising said glutamine in hyperpolarized form.

In a preferred embodiment, the mixture of step a) essentially consists of glutamine, $Rb^+$ or $Cs^+$ hydroxide, a polarizing agent and a glass forming agent.

Preferably, the mixture subjected to DNP process comprises less than 10% (w/w) of water, more preferably less than 8% and even more preferably less than 5% of water.

Preferably the hydroxide is cesium hydroxide.

Preferably the solvent is a physiologically acceptable solvent, more preferably is DMSO.

According to a preferred embodiment, the mixture of step a) is frozen, preferably at a temperature lower than 4° K, before the DNP.

Preferably the frozen hyperpolarized mixture is dissolved in an aqueous solvent, preferably water According to a preferred embodiment, the polarizing agent is completely or partially separated before administration of the hyperpolarized mixture.

Another aspect of the invention relates to a preparation comprising hyperpolarized glutamine wherein the amount of hyperpolarized glutamate and/or pyro-glutamate (by-products) in the preparation is less than 1%, preferably less than 0.8%, said amount being determined as a percentage of the total 5-$^{13}$C signal measured on the preparation.

According to another aspect, the present invention relates to a method for operating a MRI system comprising the steps of:

a) submitting a subject, which has been pre-administered with a hyperpolarized glutamine obtained according the DNP method described above and which has been positioned in said MRI system, to a radiation frequency selected to excite nuclear spin transitions in a non-zero nuclear spin nuclei of said glutamine; and b) recording a MR signal from said excited nuclei.

BRIEF DESCRIPTION OF THE DRAWINGS

FIG. 1 shows the NMR spectra of a comparative Cs-containing preparation (dotted line; (a)) and of a preparation according to the invention after Cs/Na ion exchange (continuous line; (b)).

DETAILED DESCRIPTION OF THE INVENTION

The term "polarizing agent" refers, according to the art, to compounds comprising unpaired electron which are capable, when admixed with compounds comprising MR active nuclei (e.g. $^{13}$C and/or $^{15}$N nuclei) and subjected to a DNP process (e.g. with microwave irradiation), to transfer polarization from the unpaired electron to the MR active nuclei of the compound to be polarised.

The manufacturing method of the invention allows obtaining a hyperpolarized amino acid with a remarkably low content of by-products of said amino acid, as compared to conventional aqueous based preparations of the polarized amino acid.

The Applicant has in fact observed that conventional aqueous preparations of the above amino acids with alkali metal hydroxides (as illustrated for instance in the above cited WO 2009/098191) may determine undesirable degradations of the amino acid into by-products which may negatively affect the subsequent use of the preparation as metabolic imaging agent.

In particular, as illustrated in the following reaction scheme, upon contact with water, glutamine (a) is transformed into pyroglutamic acid—or its respective pyroglutamate salt—(a1) and glutamic acid (a2) (or glutamate):

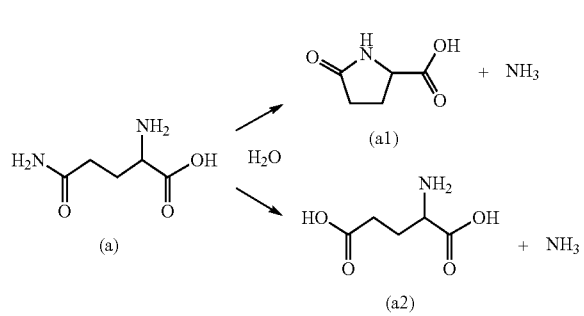

The formation of glutamine by-products in the presence of water is significantly enhanced at high (e.g. higher than 8) or low (e.g. lower than 6) pH values.

For instance, the Applicant has observed that immediately after preparation of an amino acid/sodium hydroxide aqueous mixture, already 1.7% of glutamine has been transformed in these by products, while after 5 hours from preparation said amount was higher than 3%.

Metabolic conversion of glutamine into glutamate can be used in the evaluation of tumor pathologies (see e.g. Gallagher F et al., "$^{13}$C magnetic resonance spectroscopy measurements of glutaminase activity in human hepatocellular carcinoma cells using hyperpolarized $^{13}$C-labeled glutamine", Magn. Reson. Med. 2008; 60:253-257). However, if the polarized mixture which is administered contains a certain amount of the metabolic product (i.e. glutamate), the results of the analysis may be incorrect. In addition, while pyroglutamate does not itself enter into the metabolic cycle, it provides nevertheless a chemical shift which substantially overlaps with the one of glutamate, thus further reducing the reliability of the measurements. It is thus of paramount importance that the hyperpolarized preparation which is used for the MR investigation contains very limited amounts (preferably being substantially free) of these by-products, to avoid erroneous interpretation of the results.

Glutamine

Glutamine is preferably isotopically enriched with MR active (non-zero spin) nuclei, such as $^{13}$C and/or $^{15}$N. The term "enriched" means that the concentration of the non-zero spin nuclei in the amino acid is above the typical value of natural abundance of said nuclei, preferably above at least 10% of natural abundance, more preferably above at least 25%, and even more preferably above at least 75% of its natural abundance and most preferably above at least 90% of its natural abundance. The enrichment will in particular be concentrated on an atom position, for which a chemical transformation of the molecule, or a chemical or magnetic changes of the environment of the molecule, will be measurable as a change of its chemical shift. Preferably the amino acid is enriched at the 5-position, i.e. 5-$^{13}$C-glutamine. Alternatively, also enrichment at the 1-position can be envisaged, i.e. 1-$^{13}$C-glutamine. Said non-zero nuclei confer to the amino acid a T1 relaxation time of at least 5 s (seconds), preferably of at least 10 s, more preferably of at least 20 s, even more preferably of at least 30 s, and much more preferably of at least 40 s, measured in a solution subjected to a magnetic field of from about 0.5 mT to about 20 T (Tesla), and at a temperature of from 25° C. to 70° C., in particular at a field strength of 1.5-3 T and at a temperature of 37° C. When outside the body, said T1 values are generally measured at field strength of 0.5 mT and at a temperature of 60° C. According to a further embodiment, the above mentioned non-zero spin nuclei can be directly linked to one or more Deuterium atom, for possibly prolonging the T1 values of the final hyperpolarized compound (see e.g. US 2008/0287774 A1, herein incorporated by reference). The enrichment may include either selective enrichments of one or more sites within the amino acid or uniform enrichment of all sites. To this extent, commercially available enriched amino acids can be suitably employed or, in case, the enrichment of choice can be achieved by chemical synthesis, or biological labeling, according to methods known in the art. Preferably glutamine is L-glutamine.

Hydroxide

The hydroxide of the DNP mixture of step a) is preferably in anhydrous form. Alternatively it can be used as monohydrate. In any case it is added to the mixture in dry form, i.e. not as an aqueous solution. Preferably Cesium hydroxide is used.

Polarizing Agent

The polarizing agent shall be stable and soluble in the DNP preparation in order to obtain a homogenous distribution and an optimal concentration of the electron spin relative to the nuclear spin. Typically, the polarizing agent is added in an amount of from 5 mM to 50 mM to the mixture undergoing DNP, more preferably from 8 to 18 mM.

Suitable polarizing agents are described, for instance, in WO-A-96/39367 (A radical compound of formula I

where each group Ar$^1$, which may be the same or different is an optionally substituted aromatic group, preferably an optionally substituted 5-7 membered carbocyclic or heterocyclic aromatic ring optionally carrying one or more fused carbocyclic or heterocyclic rings, preferably a benzyl ring and at least one of said Ar$^1$ groups is a group Ar$^1$ of formula

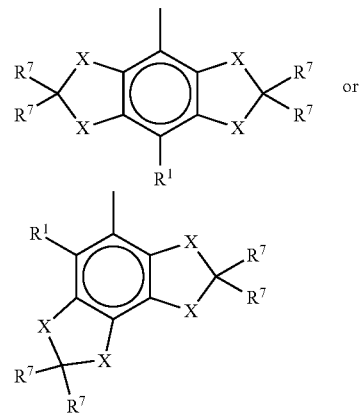

(wherein each X which may be the same or different represents an oxygen or sulphur atom or a group CO or S(O)$_n$ (where n is 1 to 3) with the proviso that at least one group X is a sulphur atom or a S(O)$_n$ group: R$^1$ represents a hydrogen atom or group of formula -M, —XM, —X—Ar$^2$, or —Ar$^2$ where M is a water solubilising group, and Ar$^2$ represents a 5-10 membered aromatic ring optionally substituted by a water solubilising group M; and each of the groups R$^7$, which may be the same or different represents a hydrogen atom, or a hydrocarbon group such as an alkyl, hydroxyalkyl, alkoxyalkyl, alkoxycarbonyl, or carbamoyl group, or a water solubilising group M or two groups R$^7$ together with the atom to which they are bound represent a carbonyl group or a 5 to 8 membered cycloalkylidene, mono- or di-oxacycloalkylidene, mono- or di-azacycloalkylidene or mono- or di-thiacycloalkylidene group optionally with the ring attachment carbon replaced by a silicon atom (preferably however in any spiro structure the ring linking atom will be bonded to no more than three heteroatoms) and $R^5$ where it is other than hydrogen, is optionally substituted by a hydroxyl group, an optionally alkoxylated, optionally hydroxylated acyloxy or alkyl group or a water solubilising group M)) or a perdeuterated analogue or salt thereof).

Preferred polarizing agents comprise trytil radicals of formula (I):

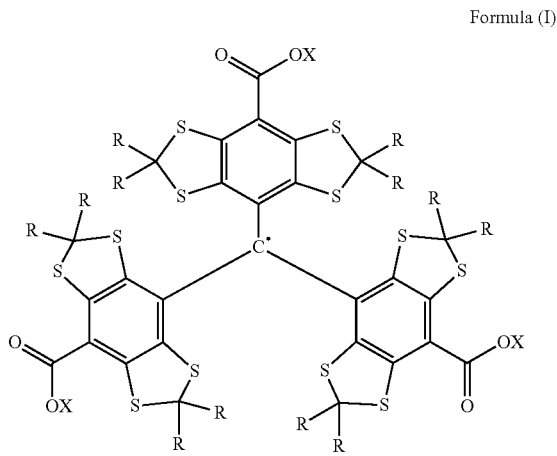

Formula (I)

wherein:

R the same or different, represents a straight chain or branched C1-C6-alkyl group optionally substituted by one or more hydroxyl group, methoxy group, or a group of formula —$(CH_2)_n$—O—R2, wherein n is 1, 2 or 3;

R2 is a straight chain or branched C1-C6-alkyl group, optionally substituted by one or more hydroxyl groups or methoxy groups; and X is independently selected from: H; an alkaline metal, e.g. Na, K, Cs; an optionally substituted straight or branched C1-C6 alkyl group, optionally interrupted by sulphur or oxygen atoms; or an optionally substituted aliphatic or aromatic C3-C8 cyclic group or hetero group.

According to an embodiment of the invention, said radical is a compound of the above formula (I) which provides a concentration of at least 5 mM in the DNP preparation, e.g. a compound of formula (I), wherein X is hydrogen, or wherein X is selected from hydrophobic moieties such as methyl, ethyl, ter-butyl or phenyl. For instance, radicals which are substantially insoluble in water can be used, e.g. a compound of formula (I), wherein both X and R are hydrophobic moieties, e.g. alkyl moieties, to allow an easy separation thereof from the polarized aqueous mixture.

Anhydrous Solvent

The anhydrous solvent employed for preparing the mixture shall be such that is capable of dissolving the components of the mixture at an acceptable concentration. In particular, the concentration of amino acid in the DNP mixture shall be of at least 1 molar (1 M) preferably of at least 2 molar (2 M) and even more preferably of at least 3 molar (3 M). The term "anhydrous" comprises solvents containing substantially no water, e.g. less than 1% (w/w), preferably less than 0.5% w/w and even more preferably less than 0.1% w/w of water, down to a maximum amount of water of e.g. 0.005% w/w.

Typically, higher polarisation levels are achieved by the DNP method when the DNP mixture forms a glass upon cooling/freezing (rather than a crystallized sample). The formation of the glass is achieved by adding a "glass-forming agent" (or "glassing agent") to the mixture, which prevents crystallization upon freezing, while promoting the formation of a frozen mixture in glass form. The fact that a component behaves as a glass-forming agent depends from many parameters, including the composition of the mixture to freeze. For instance, some compounds may behave as glass-forming agents when combined with certain compounds and/or in certain concentrations, while they will not produce the desired glassy form when admixed with different components and/or at different concentrations. Based on the common general knowledge in the field and with a minimal experimentation (e.g. by visual inspection of the mixture to be polarized after sudden freezing in liquid $N_2$ as described, for instance ba S. Colombo Serra et al., "Hyperpolarized 13C-labelled anhydrides as DNP precursors of metabolic MRI agents", Contrast Media Mol. Imaging 2012, 7, pp. 469-477), the skilled person is generally capable of determining, without undue burden, which are the suitable glass forming agents for the various mixtures to be frozen and subjected to hyperpolarization . . . . While the glass-forming agent may be an additional substance which can be added to the mixture to freeze, advantageously, the glass forming agent is the solvent (or a co-solvent) used for dissolving the components of the mixture. Accordingly, in the present invention the anhydrous solvent is preferably selected in order to also act as a glass forming agent in the DNP mixture. Particularly for in vivo applications, where the solvent is administered to a patient, the anhydrous solvent shall be physiologically acceptable (especially for humans and/or mammals) at the administered concentrations. A preferred solvent which can be used as glass forming agents and which is also physiologically acceptable is, for instance, dimethyl sulfoxide (DMSO).

DNP Mixture and Polarization Process

The above components of the DNP mixture can be admixed according to any suitable technique and methodology known in the art. In a preferred embodiment, the amino acid and the hydroxide are first admixed as dry powders. The powder mixture is then dissolved in the anhydrous solvent, which preferably already contains the polarizing agent dissolved therein. It is worth to notice that a similar procedure can not be applied with mixtures of sodium hydroxide and glutamine, as these mixtures are substantially insoluble in anhydrous solvents. Similarly, also glutamine as such has very poor solubility in anhydrous solvents. Optionally, the DNP mixture may further contain a paramagnetic metal ion, for further increasing the polarisation levels in the compound to be polarised (see e.g. WO 2007/064226 herein incorporated by reference); preferably, the paramagnetic metal ion is in the form of a complex with a chelating agent, such as, for instance DOTA, DO3A, BOPTA or DTPA; preferably the paramagnetic metal ion is a Gadolinium ($Gd^{3+}$).

As it is important that the presence of water in the mixture is kept as low as possible (to avoid or substantially limit the above mentioned formation of undesired by-products) essentially no water in free form (e.g. as a solvent) is added to the mixture. Nevertheless, as the components of the mixture may contain a certain amount of water incorporated therein, in such cases minimal amounts of water will nevertheless be contained in the mixture. For instance, anhydrous DMSO contains less than 0.005% of water by weight; furthermore, if the hydroxide is used in hydrated form, the water of hydration will then be present, at least in part, in free form in the mixture. On the other side, even in the case that the components forming the mixture are substantially free of water, once the above components have been admixed together the resulting mixture will necessarily contain a certain amount of water; as a matter of fact, this water derives from the salt-forming reaction between the hydroxide and the amino acid (e.g. 3.3% w/w of water is produced by a concentrated mixture of CsOH with glutamine in DMSO—3.3 M in glutamine). Anyhow, the total water content in the mixture undergoing hyperpolarization, either deriving from the above salt-forming reactions or incorporated in the components of the mixture, shall preferably be less than 10% w/w, with respect to the total mixture, more preferably less than 8% w/w and even more preferably less than 5%. In a particularly preferred embodiment, only the water produced by the salt-forming reaction is contained in the mixture.

The so obtained mixture is then subjected to the dynamic nuclear polarization process of step b) according to methods known in the art.

Typically, an efficient DNP process is best obtained at high magnetic field (3-8 T) and low temperatures (typically lower than 100° K, more preferably lower than 10° K, e.g. from 0.5 to 4° K, even more preferably from 0.5 to 2° K), to obtain (by microwave irradiation of the sample) a level of polarization of the sample of at least 1%, preferably of at least 5% and even more preferably of at least 10%, where polarization is defined by the following equation:

$$P = \frac{N\alpha - N\beta}{N\alpha + N\beta}$$

wherein;

$N_\alpha$ is the number of spins in nuclear spin state α; and
$N_\beta$ is the number of spins in nuclear spin state β.

In the practice, a container containing the DNP mixture is introduced into a polarizing device comprising a cryostat, means for producing a magnetic field and a microwave generator. Advantageously, dissolving means are connected with the polarizing device, in order to dissolve the polarized mixture once the desired level of polarization has been achieved. Preferably, in case the polarized sample has to be administered to a patient, the polarizing device further contains means for recovering the dissolved sample and providing it to an injection system for administration thereof.

At the end of the polarization process, the sample, typically in frozen form, can be used as such, for solid state NMR spectroscopy; the hyperpolarised solid sample may thus be analysed e.g. by static or magic angle spinning solid state NMR spectroscopy.

Preferably, however, the hyperpolarized sample is subjected to dissolution, for use in liquid MR analysis.

Dissolution of Hyperpolarized Sample

Accordingly, once the mixture has reached the desired level of polarization, the frozen sample is dissolved.

Dissolution of the sample is performed by addition of a dissolving medium, preferably an aqueous solution, for instance hot water. Preferably the dissolution is performed while the sample is maintained in the high magnetic field. Details on the dissolution process of a frozen hyperpolarised mixture and suitable devices for performing the dissolution are provided, for instance, in WO-A-02/37132.

The obtained solution containing the polarized amino acid can be used for in vitro, ex vivo and in vivo MR detection and/or imaging. Particularly, but not only, for in vivo use the pH of the solution containing the hyperpolarized amino acid may be adjusted at physiologically acceptable values by adding suitable acid or basic buffers thereto, before administration thereof. Furthermore, the polarizing agent and the optional paramagnetic metal ion are preferably completely or partially removed from the mixture before use or administration thereof, according to common methods (e.g. precipitation and filtration of the solution).

Administration

When used for in vivo applications, the precise concentration of the administered solution containing the hyperpolarized amino acid will depend upon a range of factors such as, inter alia, toxicity and administration route. In general, optimal concentrations will in most cases lie in the range from 10 mM to 150 mM, particularly from 40 to 80 mM. In any case, the dosage of the solution should be kept as low as possible whilst still providing a detectable signal of the polarized amino acid or metabolites thereof. The dosage of the hyperpolarized amino acid employed according to the present method will vary depending on, for instance, the tissue or organ of interest and the measuring apparatus. The hyperpolarized amino acid can be administered into the vascular system or directly into an organ or muscle tissue, or by subdermal or subcutaneous route, as the case may be. Then, according to the present method, the subject is exposed to a uniform magnetic field (also known as "primary magnetic field") with radiation of a frequency selected to excite nuclear spin transitions in said hyperpolarised active substrate. The hyperpolarization of the amino acid results in an increasing in the population difference between the excited and ground nuclear spin states of those nuclei which are responsible for the magnetic resonance signals. Since MR signal intensity is proportional to this population difference, the final detected MR signals result in larger amplitude signals. The amplitude of the induced MR signals is also dependent upon several other factors, such as the strength of the magnetic field, the temperature of the sample, the isotopic nature and chemical environment of the imaging nuclei and the like.

The methods for detecting MR signals are those commonly known in conventional MR scanning, such as, multinuclei scanner detection, fast single shot imaging sequences, EPI, RARE and the like. Similarly, the MR signals obtained in the method of the present invention may be conveniently converted into 2- or 3-dimensional image data, into functional, flow or perfusion data, as well as into physiological or metabolic data (e.g. pH, pCO2, temperature or ionic concentrations), by means of conventional manipulations. In particular, the metabolic conversion of the hyperpolarized amino acid may allow to study metabolic processes in the patient's body and/or provide information on metabolic state of a (healthy or pathological) tissue. It will be clear that the present method should be carried out within the frame of time in which the hyperpolarised active amino acid remains significantly polarised, shortly after dissolution of the frozen sample. Therefore, the administration of such active amino acid and the subsequent MR measurement are preferably effected as rapid as feasible. This means that the subject, either human or non-human animal body, should be available close to the area in which the polarisation takes place. It has to be noted in this respect that the physical features of the solution to be administered (such as the temperature, density and the like) have to be physiologically tolerable in order to reduce the risks associated with the selected route of administration.

Due to the versatility of the process, the method of the present invention may find clinical application in a variety of imaging investigations such as, but not limited to, the vascular/angiographic imaging, interventional applications, perfusion mapping or metabolic/molecular imaging.

The following examples will help to further illustrate the invention.

EXAMPLES

Materials

The following materials are employed in the subsequent examples:

| | |
|---|---|
| Radical 1 | (tris(8-carboxy-2,2,6,6-(tetra(hydroxyethyl)-benzo-[1,2-4,5']-bis-(1,3)-dithiole-4-yl)-methyl sodium salt |
| Radical 2 | (tris(8-carboxy-2,2,6,6-(tetra(hydroxyethyl)-benzo-[1,2-4,5']-bis-(1,3)-dithiole-4-yl)-methyl acid form |
| Gd complex 1 | 2-[4-(2-hydroxypropyl)-7,10-bis(2-oxido-2-oxoethyl)-1,4,7,10-tetrazacyclododec-1-yl]acetate, gadolinium(III) complex |
| Gd complex 2 | [[a1,a4,a7-tris[(phenylmethoxy)methyl]-1,4,7,10-tetraacetato(4-)]gadolinite(1-)]hydrogen |

Example 1—Comparative

DNP Preparation of a Sodium Hydroxide Preparation of L-Glutamine

5-$^{13}$C-L-glutamine (36 mg, 0.244 mmol) and unlabeled L-glutamine (73.0 mg, 0.5 mmol) was dissolved in Sodium hydroxide solution (12 M, 63 µl, 86.2 mg, 1 eqv.) and water (60 µl, 59.3 mg) in and Eppendorf tube. The mixture was whirl-mixed and ultra-sonicated until a clear solution was formed. The total weight of this mixture was 254.5 mg and the density was 1.2 yielding a total volume of 210 µl. To this mixture was added Radical 1 (4.9 mg, 3.4 µmol) and 4.1 mg of a stock solution of 100 µmol Gd-complex 1 solution in water. The glutamine concentration in the mixture was 3.5 M.

Example 2—Comparative

DNP Polarization Build-Up and Dissolution of Sodium Hydroxide Preparation of L-Glutamine, Immediately after DNP Preparation Three aliquots (0.23 mmol, 76 µmol $^{13}$C) of the preparation according to Example 1 were collected and used for subsequent DNP experiments. A first aliquot (sample 2a) was immediately transferred to a sample cup and the sample cup was inserted into a DNP polarizer. The other two aliquots were transferred to a sample cup after 100 minutes from preparation (sample 2b) and after 310 minutes from preparation (sample 2c), respectively, and inserted into a polarizer.

The compositions were polarized under DNP conditions at 1.2 K in a 3.35 T magnetic field under irradiation with microwave (93.905 GHz). The estimated solid-state polarization was 20% for samples 2a and 2b, and 15% for sample 2c; the polarization build-up constant was 2400 s for samples 2a and 2b, and 3000 s for sample 2c.

The respective polarized samples were dissolved in 5 ml 100 mM phosphate buffer pH 7.0+100 mg/l EDTA+20 µl 12 M HCl to neutralize the base. A time series of 1D 13C-NMR spectra were recorded with a total delay between the pulses of 3 s. The measured liquid state polarization after 12 s transfer time was 13% for samples 2a and 2b, and 9% for sample 2c. The pH in the dissolved sample was 7.4 for samples 2a and 2b, and 7.3 for sample 2c.

Table 1 illustrates the amounts of byproducts measured in the three samples.

TABLE 1

By-products in NaOH/glutamine aqueous DNP preparations

| | Sample 2a<br>T = 0 min | Sample 2b<br>T = 100 min | Sample 2c<br>T = 310 min |
|---|---|---|---|
| Total by-products (% of 5-$^{13}$C signal) | 1.7 | 2.2 | 3.1 |
| 1-$^{13}$C-Pyroglutamate (% of total) | 62 | 67 | 82 |
| 5-$^{13}$C-Glutamate (% of total) | 38 | 33 | 18 |

Example 3

DNP Preparation of a Cesium Hydroxide Preparation of L-Glutamine

5-$^{13}$C-L-glutamine (36.3 mg, 0.246 mmol), unlabeled L-glutamine (74.9 mg, 0.512 mmol) and Cesium hydroxide monohydrate (132.4 mg, 0.788 mmol) were added to an Eppendorf tube. The powders were whirl-mixed and then dissolved in a solution containing Radical 2 (9.5 mg, 7.0 µmol), Gd complex 2 (6.3 mg of a stock solution of 100 µmol/g DMSO) and anhydrous DMSO (145 µl, 159.8 mg, water content <0.1% (w/w). The mixture was whirl-mixed and ultra-sonicated until a clear solution was formed. The total weight of this mixture was 419.2 mg and the density was 1.5 yielding a total volume of 279 µl. The concentration of glutamine in the mixture was 3.3 M.

Example 4

DNP Polarization Build-Up and Dissolution of Cesium Hydroxide Preparation of L-Glutamine, Immediately after DNP Preparation Three aliquots of the preparation according to Example 3 were collected and used for subsequent DNP experiments. A first aliquot (sample 4a: 127.6 mg, 0.227 mmol, 74 µmol $^{13}$C) was immediately transferred from the Eppendorf tube to a sample cup and the sample cup was inserted into a DNP polarizer. The other two aliquots were transferred to a sample cup after 100 minutes from preparation (sample 4b: 128.2 mg, 0.228 mmol, 75 µmol $^{13}$C) and after 310 minutes from preparation (sample 4c: 128.4 mg, 0.228 mmol, 75 µmol $^{13}$C), respectively, and inserted into a polarizer.

The compositions were polarized under DNP conditions at 1.2 K in a 3.35 T magnetic field under irradiation with microwave (93.905 GHz). The estimated solid-state polarization was 25% for sample 4a, 26% for sample 4b and 27% for sample 4c; the build-up constant was 2000 s for sample 4a, 1800 s for sample 4b and 2800 s for sample 4c.

The respective samples were then dissolved in 5 ml 100 mM phosphate buffer pH 7.0+100 mg/l EDTA+20 µl 12 M HCl to neutralize the base. A time series of 1D 13C-NMR spectra were recorded with a total delay between the pulses of 3 s. The measured liquid state polarization after 12 s transfer time was 14%, 15% and 19% and the pH in the dissolved sample was 7.1, 7.2 and 6.9, respectively, for sample 4a, 4b and 4c.

Table 2 illustrates the amounts of byproducts measured in the three samples.

TABLE 2

By-products in CsOH/glutamine anhydrous DNP preparations

| | Sample 4a<br>T = 0 min | Sample 4b<br>T = 100 min | Sample 4c<br>T = 310 min |
|---|---|---|---|
| Total by-products<br>(% of 5-$^{13}$C signal) | 0.4 | 0.5 | 0.5 |
| 1-$^{13}$C-Pyroglutamate<br>(% of total) | 90 | 90 | 90 |
| 5-$^{13}$C-Glutamate<br>(% of total) | 10 | 10 | 10 |

By comparing the above results with those of table 1, it is apparent that anhydrous (i.e. with no addition of free water) DNP preparations according to the invention allow obtaining a substantial reduction of the amount of by-products produced in the mixture before undergoing the DNP process.

Example 5

DNP Polarization Preparation, Build-Up and Dissolution of Cesium Hydroxide Preparation of L-Glutamine, for Ion-Exchange of Cesium with Sodium 5-$^{13}$C-glutamine (11.5 mg, 79 µmol), unlabeled glutamine (25.7 mg, 176 µmol) and Cesium hydroxide monohydrate (45.8 mg, 272 µmol) was added to an Eppendorf tube. The powders were whirl-mixed where after they were dissolved in 48 µl (54.1 mg) of a solution prepared of Radical 2 (6.8 mg, 5.0 µmol), Gd complex 2 (4.2 mg of a stock solution of 100 µmol/g DMSO) and DMSO (106 µl, 118.0 mg). The mixture was whirl-mixed and ultra-sonicated until a clear solution was formed. The total weight of this mixture was 137.3 mg and the density was 1.5 yielding a total volume of 91.5 µl. The concentrations in the mixture were; radical 2: 23 mM, Gd complex 1: 2.0 mM and glutamine 2.8 M.

124 mg of the composition (71 µmol $^{13}$C) was transferred from the Eppendorf tube to a sample cup and the sample cup was inserted into a DNP polarizer. The composition was polarised under DNP conditions at 1.2 K in a 3.35 T magnetic field under irradiation with microwave (93.905 GHz). The estimated solid-state polarization was 25% and the polarization build-up constant was 2500 s.

The sample was dissolved in 6 ml 100 mM Tris buffer pH 8.0 at Room Temperature+100 mg/l EDTA+22 µl 12 M HCl to neutralize the base. The sample was pushed through an ion-exchange cartridge (Varian Bond Elut, SCX, 500 mg, 0.62 meq/g), which had been pre-treated with 1 column of brine followed by one column of water, into a 10 mm NMR tube. A time series of 1D 13C-NMR spectra were recorded with a total delay between the pulses of 3 s. The liquid state polarization was 4% after 35 s transfer time. The pH was 7.9 (at 37° C.) in the dissolved sample. The removal of Cesium was highly efficient. The concentration of cesium ions in the sample before exchange was approximately 50 mM while in the exchanged sample it was below the experimental detection level of 30 µM. In FIG. 1, a NMR reference spectrum of a standard sample containing 0.1 mM cesium (dotted line, a) is compared with the NMR spectrum of the hyperpolarized sample in example 5 following ion exchange from cesium to sodium (continuous line, b), showing that substantially no cesium is left in the sample after the ion exchange. The liquid state polarization following ion exchange was as expected when accounting for liquid state T1 of glutamine labeled in position 5 and the experimental time (35 s). It is furthermore estimated that glutamine was quantitatively recovered following the ion exchange.

Example 6—Comparative

DNP Polarization Preparation, Build-Up and Dissolution of Cesium Hydroxide Preparation of L-Glutamine in Water 5-$^{13}$C-L-glutamine (12.1 mg, 82 µmol), unlabeled L-glutamine (26.8 mg, 183 µmol) was dissolved in a Cesium hydroxide solution (76.0 mg, 452 µmol in water (37 µl, 36.5 mg)). 1.9 mg of radical 1 (1.3 µmol) and gadolinium complex 1 (1.4 mg of 100 µmol/g solution in water) was dissolved in 68.2 mg (105.6 mg) of the Cesium hydroxide-glutamine mixture. The mixture was whirl-mixed and ultra-sonicated until a clear solution was formed.

103.8 mg of the composition was transferred from the Eppendorf tube to a sample cup and the sample cup was inserted into a DNP polarizer. The composition was polarised under DNP conditions at 1.2 K in a 3.35 T magnetic field under irradiation with microwave (93.905 GHz). The estimated solid-state polarization was 15% and the polarization build-up constant was 2500 s.

The sample was dissolved in 5 ml 100 mM phosphate buffer pH 7.0+100 mg/l EDTA+23 µl 12 M HCl to neutralize the base. A time series of 1D 13C-NMR spectra were recorded with a total delay between the pulses of 3 s. The measured liquid state polarization was 10% after 12 s transfer time. The pH was 6.9 in the dissolved sample. The ratio of the combined byproducts (pyroglutamate and glutamate) to L-glutamine labeled in position 5 was 1.1%, which is almost three times as much as for sample 4a of the anhydrous preparation.

The invention claimed is:

1. A method for manufacturing hyperpolarized glutamine, which comprises the steps of:
  (a) admixing (i) glutamine and (ii) Rb$^+$ or Cs$^+$ hydroxide as dry powders to prepare a powder mixture;
  (b) preparing an initial mixture by admixing the powder mixture of step (a) with (iii) a polarizing agent and (iv) an anhydrous solvent, wherein essentially no water in free form is added to the initial mixture; and
  (c) subjecting the initial mixture to a dynamic nuclear polarization (DNP) process to obtain a hyperpolarized mixture comprising said glutamine in hyperpolarized form.

2. The method according to claim 1 wherein said anhydrous solvent is a glass forming agent.

3. The method according to claim 2 wherein the initial mixture consists essentially of glutamine, Rb$^+$ or Cs$^+$ hydroxide, a polarizing agent and an anhydrous solvent.

4. The method according to claim 2 wherein the initial mixture subjected to the DNP process of step (c) comprises less than 10% (w/w) of water.

5. The method according to claim 4 wherein said amount of water is less than 8%.

6. The method according to claim 4 wherein said amount of water is less than 5%.

7. The method according to claim 1 wherein the initial mixture subjected to the DNP process of step (c) comprises less than 10% (w/w) of water.

8. The method according to claim 7 wherein said amount of water is less than 8%.

9. The method according to claim 7 wherein said amount of water is less than 5%.

10. The method according to claim 7 wherein the anhydrous solvent contains less than 1% w/w of water.

11. The method according to claim 10 wherein the anhydrous solvent contains less than 0.5% w/w of water.

12. The method according to claim 10 wherein the anhydrous solvent contains less than 0.1% w/w of water.

13. The method according to claim 10 wherein the anhydrous solvent contains a maximum amount of 0.005% w/w water.

14. The method according to claim 1 wherein the anhydrous solvent is dimethylsulfoxide (DMSO).

15. The method according to claim 14 wherein the hydroxide is $Cs^+$ hydroxide.

16. The method according to claim 1 wherein the hydroxide is $Cs^+$ hydroxide.

17. The method according to claim 1 wherein the initial mixture of step (b) is frozen, at a temperature lower than 4° K, before the DNP process.

18. The method according to claim 17 wherein the hyperpolarized mixture of step (b) is in frozen form.

19. The method according to claim 18 which further comprises the step of dissolving the frozen hyperpolarized mixture of step (c) in an aqueous solvent.

20. The method according to claim 19 wherein the polarizing agent is completely or partially separated from the dissolved hyperpolarized mixture.

21. The method according to claim 1, wherein the polarizing agent is a trityl radical.

22. A method for MRI imaging comprising the steps of:
(a) admixing (i) glutamine and (ii) $Rb^+$ or $Cs^+$ hydroxide as dry powders to prepare a powder mixture;
(b) preparing an initial mixture by admixing the powder mixture of step (a) with (iii) a polarizing agent and (iv) an anhydrous solvent, wherein essentially no water in free form is added to the initial mixture;
(c) subjecting the initial mixture to a dynamic nuclear polarization (DNP) process to obtain a hyperpolarized mixture comprising said glutamine in hyperpolarized form;
(d) administering said hyperpolarized mixture to a subject;
(e) positioning the subject in a MRI system;
(f) submitting the subject to a radiation frequency selected to excite nuclear spin transitions in a non-zero nuclear spin nuclei of said glutamine; and
(g) recording a MR signal from said excited nuclei.

23. The method according to claim 22 wherein the anhydrous solvent is dimethylsulfoxide (DMSO) and the hydroxide is $Cs^+$ hydroxide.

* * * * *